United States Patent [19]
Wnek et al.

[11] Patent Number: 5,326,890
[45] Date of Patent: Jul. 5, 1994

[54] SULFONATED SILICONES AND METHODS FOR THEIR PRODUCTION

[75] Inventors: Gary E. Wnek, Latham; Jun-Kang Liu, Troy, both of N.Y.

[73] Assignee: Rensselaer Polytechnic Institute, Troy, N.Y.

[21] Appl. No.: 962,143

[22] Filed: Oct. 16, 1992

[51] Int. Cl.$^5$ ............................................. C07F 7/08
[52] U.S. Cl. ...................................... 556/11; 556/428; 528/25; 528/32; 528/41
[58] Field of Search .................... 556/428, 11; 528/25, 528/32, 41

[56] References Cited

U.S. PATENT DOCUMENTS

| | | | |
|---|---|---|---|
| 3,220,972 | 11/1965 | Lamoreaux | 260/46.5 |
| 3,715,334 | 2/1973 | Karstedt | 260/46.5 |
| 3,775,452 | 11/1973 | Karstedt | 260/429 |
| 4,288,345 | 9/1981 | Ashby et al. | 252/431 |
| 4,777,277 | 10/1988 | Colas et al. | 556/428 X |
| 4,849,127 | 7/1989 | Maxon | 556/428 X |
| 5,021,808 | 12/1991 | Autberg et al. | 556/11 X |
| 5,068,380 | 11/1991 | Meguriya et al. | 556/428 |

OTHER PUBLICATIONS

Zhou et al. "Cation transport polymer electrolytes. Siloxane comb polymers with pendant oligo-oxyethylene chains and sulphonate groups" *Polym. Comm.* 30, 52-54 (1989).
Liu and Wnek "Novel Synthesis of Sulfonated Silicones" *Polym. Prepr.*, 33, 970-972 (1992).
Yang and Wnek "Synthesis of Polysiloxanes Bearing Polar Groups" *Polymer Prepr.* 30 177 (1989).

*Primary Examiner*—Paul F. Shaver
*Attorney, Agent, or Firm*—Heslin & Rothenberg

[57] ABSTRACT

A process for the preparation of sulfonated silicones is disclosed. The process comprises the steps of (a) hydrosilylating an olefin-terminal silylketene acetal with a hydrosiloxane; (b) treating the ketene acetal with a trialkylsilylsulfonyl chloride and (c) hydrolyzing the resulting α-trialkylsilyl ester to provide a salt of an α-sulfonate. Useful products of the process are also disclosed; they comprise several genera of α-sulfonate esters pendant from siloxanes and polysiloxanes. The products are useful as polymer electrolytes and as sustained or controlled release substrates for the administration of medicines.

40 Claims, No Drawings

SULFONATED SILICONES AND METHODS FOR THEIR PRODUCTION

STATEMENT AS TO RIGHTS UNDER FEDERALLY SPONSORED RESEARCH

This invention was made with support under Defense Advanced Research Projects Agency, Grant No. B-41-C-011-DAR09. Accordingly, the U.S. Government has certain rights in the invention.

BACKGROUND OF THE INVENTION

1. Field Of The Invention

The invention relates to sulfonated silicone polymers having improved solubility and electrical properties. It also relates to methods for synthesizing the sulfonated silicone polymers.

2. Information Disclosure

Polysiloxanes, or silicones, have received much attention as specialty polymers since their commercial application in the 1940's and are by far the most important of the inorganic backbone polymers. Interest in these systems has developed as a result of their unique properties, which include low glass transition temperatures ($T_g$s), good thermal and oxidative stability, low surface energies, excellent biocompatibility and high gas permeabilities. There is considerable special interest in polysiloxanes that carry ionic substituents in their side chains because they offer promise as polymer electrolytes for solid state batteries and because they may provide water-soluble polymers for biomedical applications.

Zhou, Kahn and Smid [*Polym. Comm.* 30, 52-54 (1989)] have reported a synthesis of siloxane comb polymers with pendant sulfonate groups. A resulting polymer was reported to exhibit a glass transition temperature of $-65°$ C. and a conductivity of $10^{-5}$ ohm$^{-1}$ cm$^{-1}$ in the presence of one equivalent of tetraethylene glycol at 50° C. The synthesis of the sulfonated silicone proceeded by opening an expoxy-functionalized silicone with $Na_2S_2O_5$:

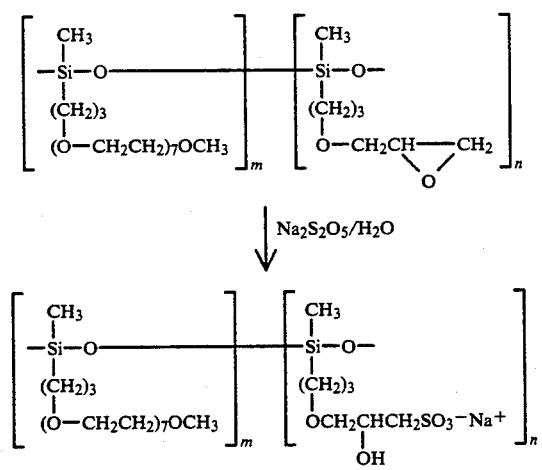

The reaction suffers from three major drawbacks: (1) The initial polymer, before sulfonation, must be water soluble; (2) the reaction is slow, requiring a reaction time of "at least 3 days"; and (3) products are limited to those arising from epoxides.

There is thus a need for an improved synthesis of silicones bearing pendant sulfonate groups. There is also a need for improved sulfonated silicones.

SUMMARY OF THE INVENTION

It is an object of the invention to provide an improved synthesis of silicone polymers having pendant sulfonate groups.

It is a further object to provide a synthesis of sulfonated silicone polymers that can be carried out efficiently on water-insoluble silicone starting materials.

It is a further object to provide sulfonated silicone polymers having good electrical conductivities.

It is a further object to provide sulfonated silicone polymers having a good balance between water solubility and lipid solubility.

These and other objects, features and advantages are realized in the instant invention which is described below.

In one aspect the invention relates to a process for the preparation of sulfonated silicones comprising the steps of:

(a) reacting a silicone having Si—H bonds with an olefin-terminated (trialkylsilyl)ketene acetal of formula

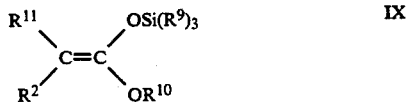

wherein
$R^2$ is hydrogen or lower-alkyl;
$R^9$ is lower-alkyl; and
one of
$R^{10}$ and $R^{11}$ is alkyl and the other is an olefin-terminal linear or branched alkylene, phenylene or naphthylene radical;

in the presence of a hydrosilylation catalyst to produce a silicone attached to the ketene acetal at the terminal carbon of the olefin-terminated radical $R^{10}$ or $R^{11}$;

(b) treating the ketene acetal attached to the silicone with a trialkylsilylsulfonyl chloride to produce an α-trialkylsilylsulfonyl ester; and (c) hydrolyzing the α-trialkylsilysulfonyl ester with a mild base to provide a salt of an α-sulfonate.

Preferably, the hydrosilylation catalyst is platinum divinyltetramethyldisiloxane, the trialkylsilylsulfonyl chloride is trimethylsilylsulfonyl chloride, and the mild base is aqueous sodium bicarbonate.

Throughout this document, each of the R groups is defined when initially presented, and the definition is retained thereafter.

In a further process aspect the invention relates to a process for the preparation of sulfonated silicones comprising the steps of:

(a) reacting a silicone having Si—H bonds with an olefin-terminated α-trialkylsilyl sulfonyl ester of formula X:

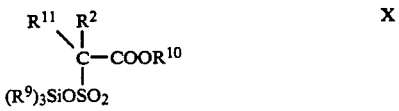

in the presence of a hydrosilylation catalyst to produce a silicone attached to the sulfonyl ester at the terminal carbon of the olefin-terminated radical $R^{10}$ or $R^{11}$; and (b) hydrolyzing the α-trialkylsilyl sulfonyl ester with a mild base to provide a salt of an α-sulfonate.

The preferred catalyst, chloride and base are as before.

In a further process aspect the invention relates to a process for the preparation of sulfonated silicones comprising the steps of:

(a) reacting a silicone having Si—H bonds with an olefin-terminated ester of formula XXII

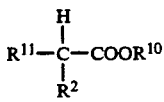

in the presence of a hydrosilylation catalyst to produce a silicone attached to the ester at the terminal carbon of the olefin-terminal radical $R^{10}$ or $R^{11}$;

(b) treating the ester with a strong base followed by a trialkylsilyl halide to form a ketene acetal;

(c) treating the ketene acetal with a trialkylsilyl sulfonyl chloride to produce an α-trialkylsilyl-sulfonyl ester; and (d) hydrolyzing the α-trialkylsilyl sulfonyl ester with a mild base to provide a salt of an α-sulfonate.

In another aspect the invention relates to useful compounds arising from the process of the invention. In this aspect the invention relates to compounds of formula I:

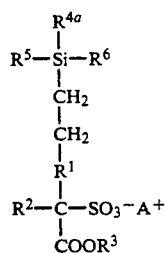

wherein
  $R^1$ is phenylene, naphthylene, or linear or branched alkylene;
  $R^2$ is hydrogen or lower-alkyl;
  $R^3$ is alkyl;
  $R^{4a}$ is lower-alkyl, lower-alkoxy, or tri(lower-alkyl)-siloxy;
  $R^5$ and $R^6$ are independently chosen from the group consisting of

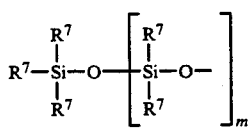

$R^7$ is lower-alkyl;
  m is zero or an integer from 1 to 100; and
  $A^+$ is hydrogen, alkali metal, ammonium or tetra(-lower-alkyl)ammonium.

$R^1$ is preferably methylene; $R^2$ is preferably lower-alkyl, most preferably methyl, $R^3$ is preferably methyl or ethyl; $R^{4a}$ and $R^7$ are preferably methyl; and $A^+$ is preferably sodium. One preferred series of compounds are those in which m is zero. Lower-alkyl, as used herein, refers to linear, branched, or cyclic hydrocarbon radicals of one to six carbons. Alkyl refers to hydrocarbon radicals of one to twenty carbons.

The invention also relates to the corresponding series of siloxanes (II) in which the α-sulfonate ester is attached through the side chain of the ester moiety rather than the side chain of the carboxylate:

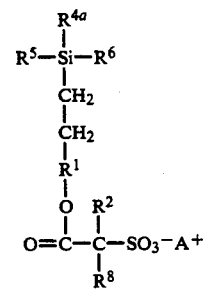

$R^8$ is hydrogen or alkyl, preferably lower-alkyl, most preferably methyl.

The invention also related to random copolymers of carbon-linked α-sulfonate esters of formula III and their corresponding oxy-linked sulfonates IV:

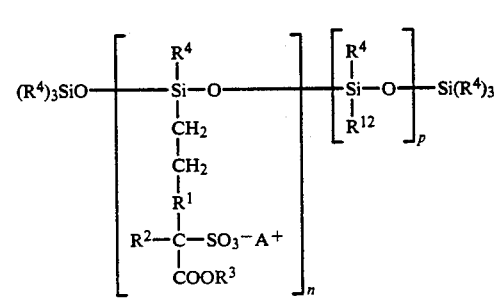

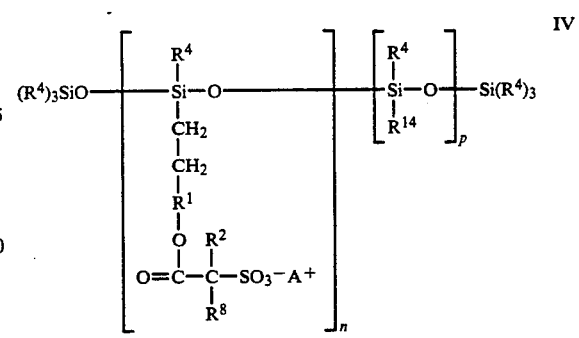

wherein $R^{12}$ is lower-alkyl or —$CH_2CH_2$—$R^{13}$ is where $R^{13}$ is hydrogen, lower-alkyl, ferrocenyl, poly(alkyleneoxy) or —$R^1$—$CH(R^2)COOR^3$; n is an integer from 2 to 2000, preferably 30 to 40 and p is zero or an integer from 1 to 2000, preferably 30 to 40. Preferred classes of copolymers are those in which the ratio of n to p is 48:52 and 30:70; another preferred polymer is that in which p is zero. Preferred residues for $R^1$, $R^2$, $R^3$, $R^4$, $R^7$, $R^8$ and $A^+$ are as before. $R^{12}$ and $R^{14}$ are preferably methyl or n-hexyl.

The invention also relates to random copolymers of carbon-linked α-sulfonate esters of formula V and their corresponding oxy-linked sulfonates VI:

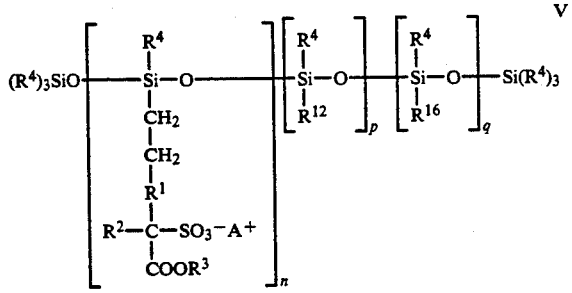

V

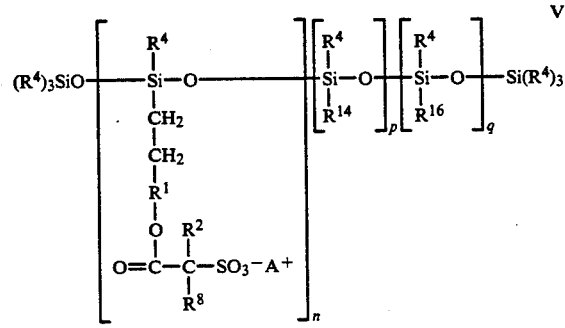

VI wherein $R^{14}$ is lower-alkyl or $CH_2CH_2R^{15}$ where $R^{15}$ is hydrogen, lower-alkyl, ferrocenyl, poly(alkyleneoxy) or $-R^1-OC(O)CH_2R^2R^8$; $R^{16}$ is lower alkyl and q is an integer form 2 to 2000. Preferred classes of copolymers are those in which the ratio of n:p:q is 46:39:15, as well as those in which $R^{15}$ is ferrocenyl and those in which $R^{16}$ is methyl.

In a further aspect, the invention relates to cyclic silicones containing carbon-linked or oxy-linked α-sulfonate esters of formulas VII and VIII:

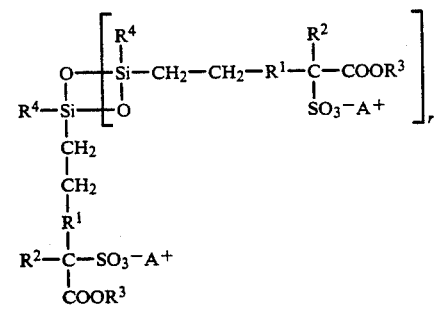

VII

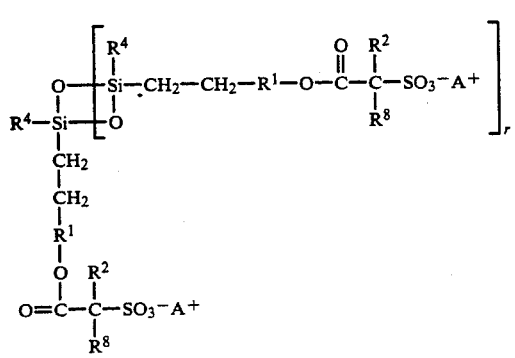

VIII wherein r is an integer from 3 to 5, preferably 3.

DETAILED DESCRIPTION INCLUSIVE OF PREFERRED EMBODIMENTS

Hydrosilylation of olefins represents a well known transformation of siloxanes whereby substituents on an olefin may be introduced into the siloxane:

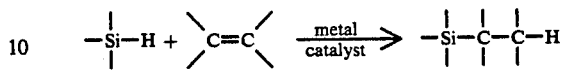

Terminal olefins react much more rapidly than internal olefins, and for this reason the hydrosilylation will proceed as desired below when the olefin is terminal. When the olefin is internal, the reaction of the ketene acetal double bond begins to compete for the Si—H and the reaction is not satisfactory.

The reaction is catalyzed by metals, usually platinum, palladium or rhodium species, but cobalt, iridium, iron and nickel catalysts are also known. Examples of the conditions for the reaction with numerous catalysts are found in the patent literature, e.g. U.S. Pat. Nos. 2,637,738; 2,851,473; 3,159,601; 3,197,432; 3,220,972; 3,419,593; 3,546,266; 3,715,334; 3,775,452; 3,814,730; 3,864,372; 4,288,345; 4,398,010; 4,503,160; 4,803,244; 4,827,009; 4,965,386; and 4,992,573. We have found that chloroplatinic acid and platinum divinyl tetramethyldisiloxane provide good yields of the desired adducts when the olefins of the present invention are used. The reactions are carried out in inert non-polar solvents such as xylene and toluene at ambient temperature to 150°.

For the purposes of the present invention, the side chain of the olefin is modified to allow the introduction of a precursor to an α-sulfonate ester. Thus, a trialkylsilylketene acetal having an olefin in the side chain (XI) may be added to a silane, according to Scheme A, to produce a Scheme A

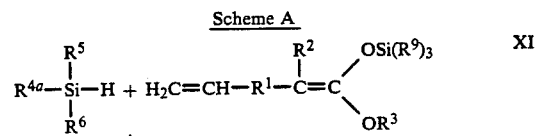

XI

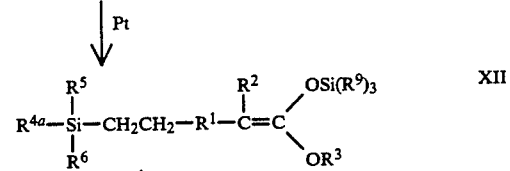

XII

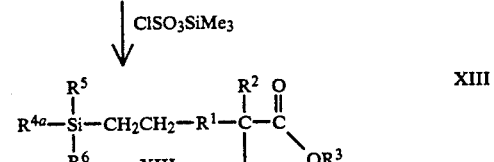

XIII

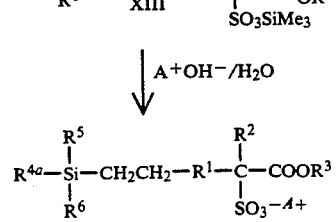

silylethyl-linked ketene acetal of formula XII. The ketene acetal (XII) is then reacted with trimethylsilylsulfonyl chloride in an inert solvent, preferably dichloroethane, to produce an α-trimethylsilylsulfonyl ester of formula XIII, which is then hydrolyzed under very mild conditions with aqueous base, preferably sodium bicarbonate at ambient temperature, to produce the sulfonated ester I.

It is contemplated that the first two steps can be performed in reversed sequence: the olefin trialkylsilylketene acetal (XI) can be reacted with trimethylsilylsulfonyl chloride and the resulting olefinic α-trimethylsilylsulfonyl ester reacted with the siloxane to yield the ester XIII.

It is further contemplated that the intermediate XII can be cynthesized by initial hydrosilylation of an olefin-terminal ester having an α-proton (XXIII)

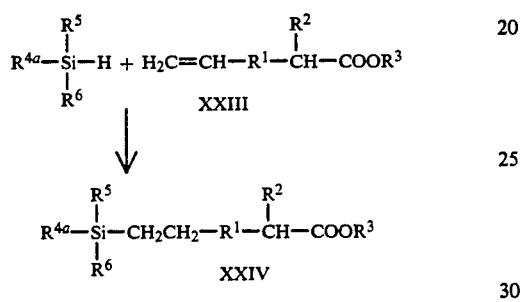

The ester XXIV can then be converted to the ketene acetal XII u sing lithium diisopropylamide and trimethylsilyl chloride according to the procedure of Ainsworth and Kuo [*J. Organametal. Chem.* 46, 73 (1972)].

By varying the hydrosilyl starting material, one may synthesize siloxanes of varying types. When $R^4$ is methyl or other lower-alkyl and $R^5$ and $R^6$ are polysiloxane residues, linear polysiloxanes having a single pendant polar group are produced. A particularly attractive class of copolymers is formed when the starting material is a polysiloxane having multiple Si—H bonds. For example, as shown in Scheme B, a poly(alkylhydrosiloxane) of s repeating units can be derivatized in an analogous fashion to the procedure of Scheme A:

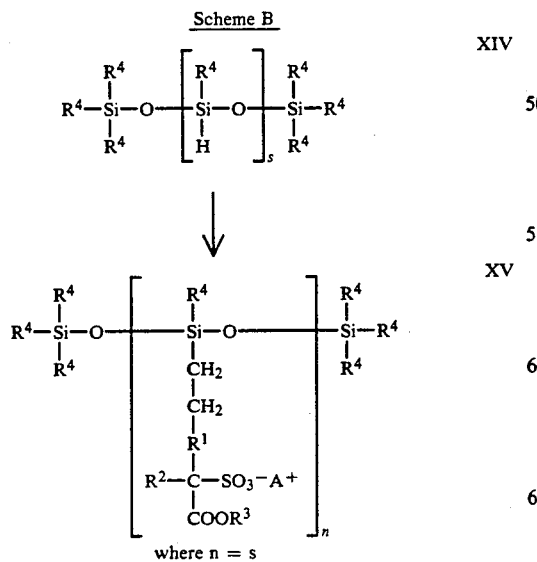

Moreover, by using mixtures of olefins in the hydrosilylation reaction, one can make random copolymers. Binary mixtures produce binary copolymers:

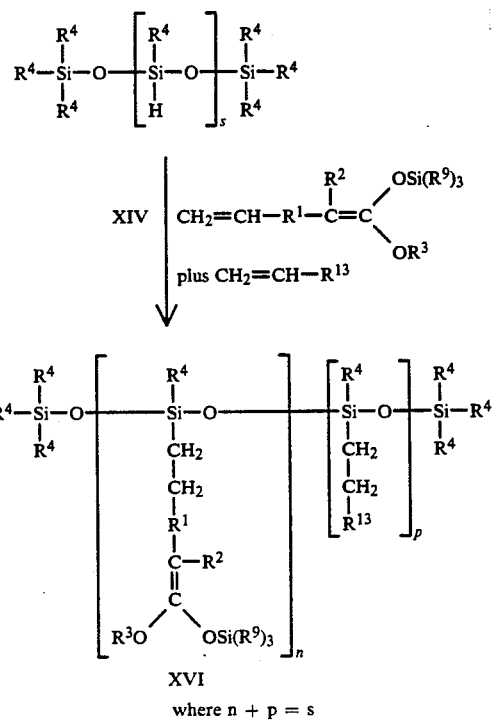

Ternary copolymers arise from sequential reaction to form a binary copolymer followed by an excess of a single olefin to cap the remaining Si—H sites:

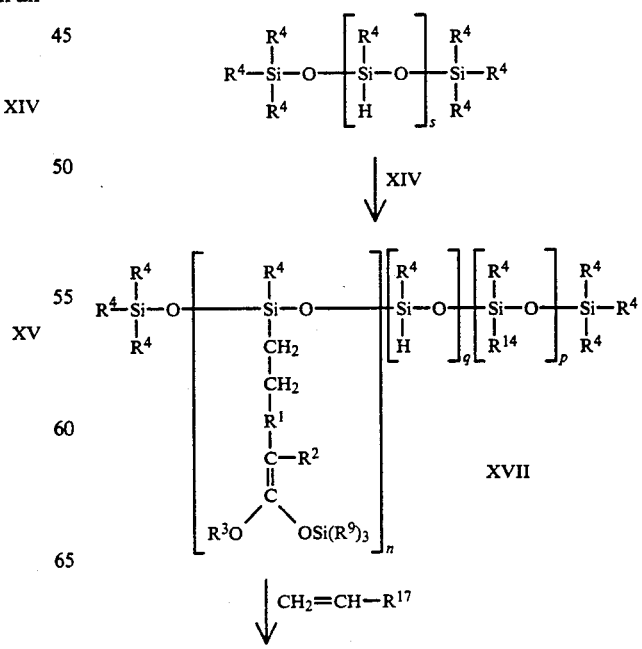

-continued

Scheme D

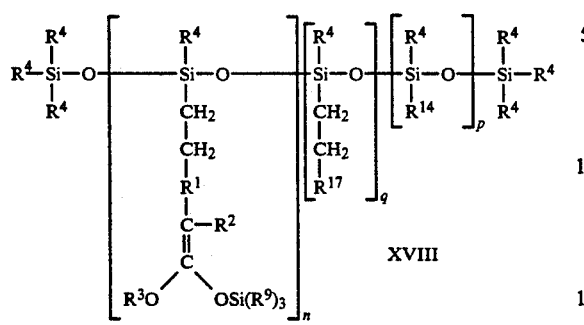

XVIII wherein $R^{17}$ is $C_1$ to $C_4$ alkyl. Alternatively, binary and ternary copolymers where $R^{12}$, $R^{14}$ or $R^{16}$ is methyl can be made by reacting the appropriate olefin or olefin mixture with a methyl hydrodimethylsiloxane copolymer.

The copolymers XVI and XVIII are then converted to the corresponding sulfonated copolymers III and V by treatment with trimethylsilylsulfonyl chloride followed by mild base. In principle, the sequence of hydrosilylation and conversion of the ketene acetal to the α-sulfonate ester could be rearranged, but the sequence shown is preferred. The preferred sequence maintains the lipid character of the polymer until the last step when the hydrophilic or amphiphilic character is finally released. The physical properties of the amphiphilic polymers would often interfere with convenient handling and workup if done in another order.

In the sequences shown above leading to the compounds of formulas I, XV, XVI and XVIII, the olefin which is hydrosilylated is in the side chain of the acid portion of the ultimate ester. The invention is not restricted to such compounds, and a parallel series of α-sulfonate esters can be made from esters in which the terminal olefin is found in the alcohol portion of the ester. Thus, Scheme E mirrors Scheme A:

Scheme E

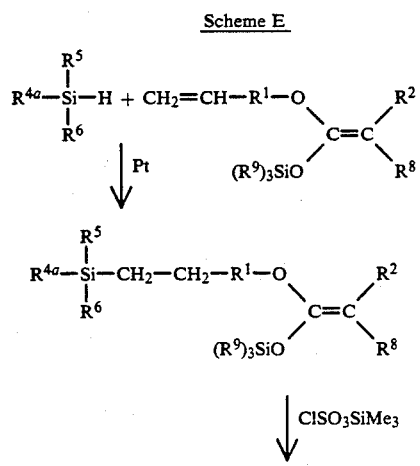

-continued

Scheme E

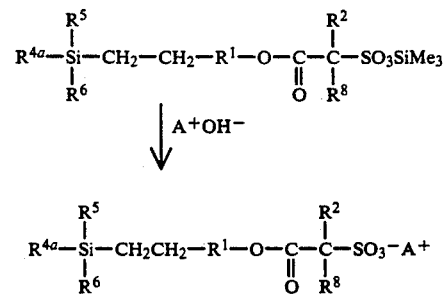

XXI

By analogous procedures, the sequence can be extended to provide polymeric oxygen-linked sulfonate esters; thus the genus IV is produced by analogy to Scheme C and the genus VI by analogy to Scheme D.

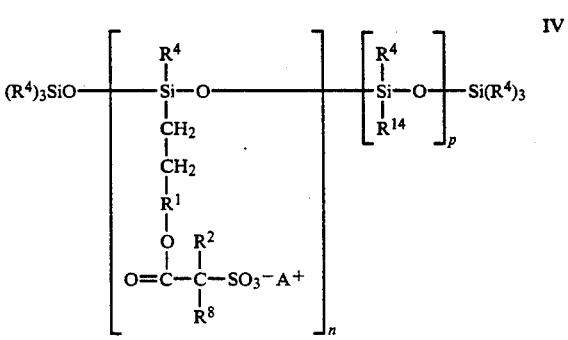

IV

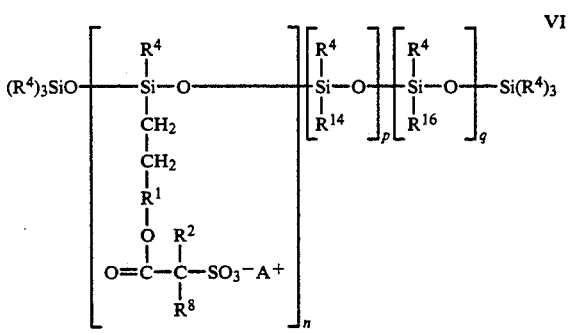

VI

In both series (oxygen-linked and carbon-linked), the classes of compounds wherein $R^{13}$ or $R^{15}$ is ferrocenyl or poly(alkyleneoxy) are particularly useful as polymeric electrolytes.

The compounds of formulas VII and VIII, having cyclic siloxane backbones, are made in analogous fashion to the linear polymers:

Scheme F

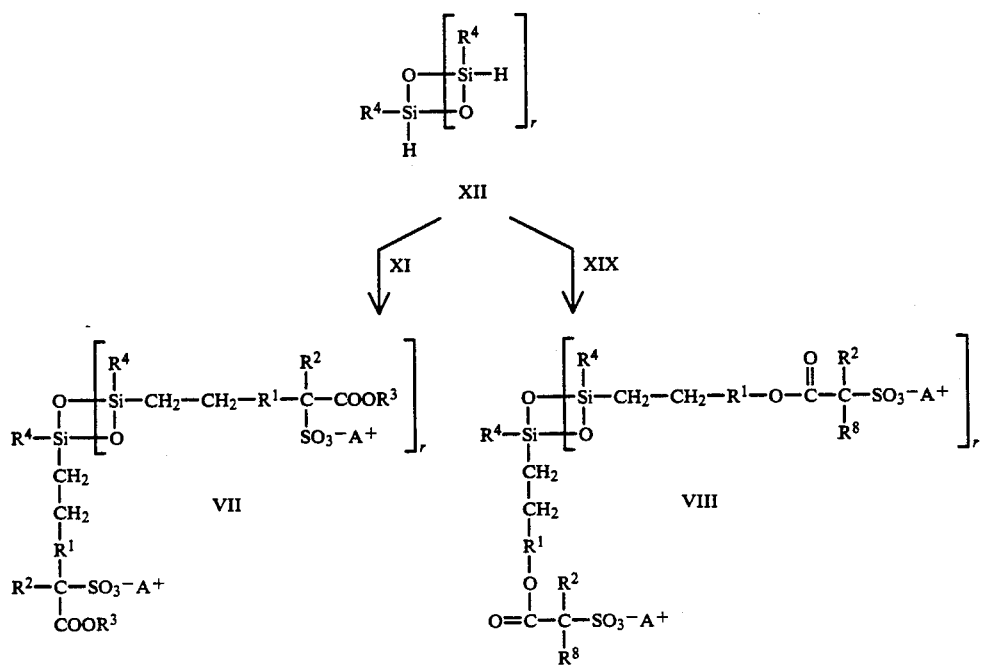

A generic description of the overall process is shown in Scheme G:

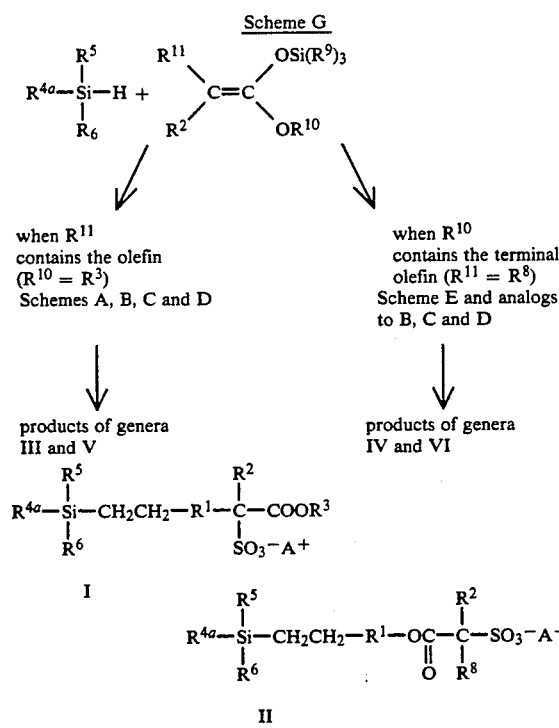

The hydrosiloxanes, which are the starting materials for the synthesis, are made by processes well known in the art; many of them are commercially available.

The ketene acetals, which are the other starting materials for the process of the invention, are synthesized by known methods. Those described by Liu and Wnek in Polymer. Prepr. 33, 970–971 (1992) and by Yang and Wnek in Polymer. Prepr. 30, 177 (1989), which are incorporated herein by reference, are preferred.

EXAMPLES

Poly(methyl hydrosiloxane) (PMHS) was acquired from Petrarch and had a number average molecular weight of approximately 4500–5000 g/mol according to the supplier. Platinum divinyl tetramethyl disiloxane complex was acquired from Petrarch and stored in refrigerator. Trimethylsilyl chloride (TMSCl), ethyl 2-methyl-4-pentenoate and methyl trimethylsilyldimethylketene acetal (MTDA) were acquired from Aldrich and distilled prior to use. Trimethylsilylsulfonyl chloride, lithium diisopropylamide, sodium bicarbonate, anhydrous dichloroethane and anhydrous ether were acquired from Aldrich and used as received. Toluene and THF were distilled from sodium benzophenone. Elemental analyses and NMR spectra were used to characterize the products.

Representative Syntheses of Starting Materials

Ethyl Trimethylsilyl 2-Methyl-2-Alkylketene Acetal (ETMA)

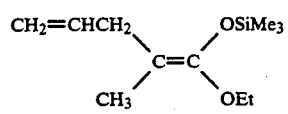

A 500 mL three-necked round-bottomed flask was fitted with a reflux condenser, magnetic stirring bar, rubber septum and a gas inlet. The apparatus was connected through the gas inlet into an argon source and reflux condenser to a bubble. After the flask was flame-dried and flushed with argon, it was charged with 250 mL of THF and distilled diisopropylamine (30.2 mL, 214.9 mmol). The flask was immersed in an ice-salt bath and cooled to −10° C., and over a period of ∼5 min, 2.5 M n-butyllithium in hexane (86.0 mL, 214.9 mmol) was added dropwise, with continuous stirring, with a syringe through the septum. After an additional 20 min of stirring, ethyl 2-methyl-4-pentenoate (35 mL, 214.9 mmol) was added dropwise through an addition funnel over a 10 min period. The solution was stirred for an additional 30 min at 0° C. At this point, distilled trimethylsilyl chloride (40.9 mL, 322.1 mmol) was rapidly introduced with a syringe through the septum. After the addition was complete (~30 s) the solution was stirred for an additional 1 h at room temperature. Solvent was removed using a rotary evaporator and the residue was treated with 200 mL of pentane. The slurry was filtered and the filtrate was concentrated on a rotary evaporator and then distilled at reduced pressure. The product, ethyl trimethylsilyl 2-methyl-2-allylketene acetal, was distilled at 79° C. (15 mm). The yield was 97%.

3-Butene-Trimethylsilyl 2,2-Dimethyl Ketene Acetal (BTDA)

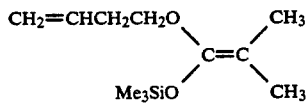

Following the same procedure, 3-butenyl isobutyrate was converted to BTDA. The yield was 94%. The product, referred to as BTDA, was distilled at 69-74° C. The 3-butenyl isobutyrate was obtained as follows: A 250 mL three neck round bottom flask was fitted with a magnetic stirring bar, rubber septum and a Dean-Stark trap on the top of which a condenser was mounted. The flask was charged with 25 g (0.35 mol) of 3-butene-1-ol, 177.5 g (1.75 mol) of methyl isobutyrate and 4.5 g potassium carbonate, and was heated to 110° C. After reaction for 40 hours, the product was collected at 145° C. by distillation. The yield was 95%.

Representative Syntheses of Products

Example 1

Sulfonated Trisiloxane XV ($R^1$=$CH_2$, $R^2$=$R^4$=$CH_3$, $R^3$=Et).

To a mixture of bis(trimethylsiloxy) methyl silane BTMS (0.12 mol) and ETMA (0.1 mol) in 100 mL dry toluene, several drops of platinum divinyltetramethyldisiloxane solution (3% in xylene) was added. The mixture was heated at 60° C. for 24 hours. Solvent and unreacted BTMS were removed at reduced pressure, and the resulting liquid was kept under 7 mm Hg for 24 hours. The product was referred to as BMSEA.

To a solution of BMSEA (20 mmol) in 100 mL anhydrous dichloroethane in a dry box, trimethylsilylsulfonyl chloride (20 mmol) was added dropwise. The reaction mixture was allowed to stand for 4 hours in a dry box while the reaction was followed by IR spectroscopy. Dichloroethane and byproducts were removed using a rotary evaporator and the reaction was kept at 70° C., 4 mm Hg for another 2 hours. The product was referred as SEA.

To a saturated sodium bicarbonate aqueous solution, SEA was added dropwise with continuous stirring until the pH was 7. Water was removed by rotary evaporator and the reaction was kept under 4 mm Hg at 60° C. for overnight. The product was obtained as a white solid which was referred to as SSEA.

Example 2

Sulfonated trisiloxane IV ($R^1$=$CH_2$, $R^2$=$R^4$=$R^8$=$CH_3$, n=1, p=0).

To a mixture of bis(trimethylsiloxy)methyl silane BTMS (0.12 mol) and BTDA (0.1 mol) in 100 mL dry toluene, several drops of platinum divinyl tetramethyl disiloxane solution (3% in xylene) was added. The mixture was heated at 60° C. for 24 hours. Solvent and unreacted BTMS were removed at reduced pressure and the resulting liquid was kept under 7 mm Hg for 24 hours. The product was referred to as BMSBA.

To a solution of BMSBA (20 mmol) in 100 mL anhydrous dichloroethane in a dry box, trimethylsilylsulfonyl chloride (20 mmol) was added dropwise. The reaction mixture was allowed to stand for 3 hours in a dry box while the reaction was followed by IR. Dichloroethane and byproducts were removed using a rotary evaporator and the reaction was kept at 70° C., 4 mm Hg for another 2 hours. The product was referred as SBA.

To a saturated sodium bicarbonate aqueous solution, SBA was added dropwise with continuous stirring until the pH was 7. Water was removed by rotary evaporator and the reaction was kept under 4 mm Hg at 60° C. for overnight. The product was obtained as a white solid which was referred to as SSBA.

Example 3

Sulfonated polysiloxane III ($R^1$=$CH_2$, $R^2$=$R^4$=$CH_3$, $R^3$=Et, $R^{12}$=$C_6H_{13}$, n=75-83, p=1-5)

To a mixture of PMHS (6 g, 100 mmol) and ETMA (21.4 g, 100 mmol) in 100 mL dry toluene, several drops of platinum divinyltetramethyldisiloxane solution (3% in xylene) was added. The mixture was heated at 60° C. for 48 hours. The extent of reaction was followed by IR spectroscopy. The remaining Si—H groups were reacted in a similar fashion for an additional 6 hours by adding a slight excess of 1-hexene. Solvent and unreacted ETMA were removed at reduced pressure with a rotary evaporator and the resulting liquid was kept under high vacuum for 24 hours. The product, referred to as PSEA, was a light yellow, viscous liquid.

A 100 mL one-necked round bottomed flask was baked by flame and flushed with dry argon, then equipped with a magnetic stirring bar in a dry box. The flask was charged with 50 mL of anhydrous dichloroethane and ETMA modified polysiloxane (20 mmol). After that, trimethylsilylsulfonyl chloride (5.0 g, 26.5 mmol) was added dropwise, with continuous stirring, over a 30 min period. The solution was stirred for an additional 4 hours. Solvent and unreacted trimethylsilylsulfonyl chloride were removed by distillation at reduced pressure. The resulting polymer, abbreviated as PSESO$_3$TMS, was a light brown, viscous liquid.

To a 200 mL saturated aqueous sodium bicarbonate solution, PSESO$_3$TMS was added dropwise with continuous stirring. After addition, the solution was concentrated on a rotary evaporator. To remove excess sodium bicarbonate, the product, sulfonated silicone PSESO$_3$Na, was purified by repeated dialysis using 1000 MW cut-off membrane for 10 days. After that, the polymer was dried by azeotropic distillation with benzene and then kept in a vacuum oven at 60° C. for 4 days.

Example 4

Sulfonated polysiloxane IV ($R^1$=CH$_2$, $R^2$=$R^4$=$R^8$= CH$_3$, $R^{14}$=C$_6$H$_{13}$, n=75-83, p=1-5)

To a mixture of PMHS (6 g, 100 mmol) and BTDA (21.4 g, 100 mmol) in 100 mL of dry toluene, several drops of platinum divinyltetramethyldisiloxane solution (3% in xylene) was added. The mixture was heated at 60° C. for 48 hr. The extent of reaction was followed by IR spectroscopy. The remaining Si—H groups were reacted in a similar fashion for an additional 6 hours by adding a slight excess of 1-hexene. Solvent and unreacted BTDA were removed at reduce pressure with a rotary evaporator first, and the resulting liquid was kept under high vacuum for 24 hours. The product, referred to as PSBA, was a light yellow, viscous liquid.

A 100 mL one-necked round bottomed flask was baked by flame and flushed with dry argon, then equipped with a magnetic stirring bar in a dry box. The flask was charged with 50 mL anhydrous dichloroethane and BTDA modified polysiloxane (20 mmol). After that, trimethylsilylsulfonyl chloride (5.0 g, 26.5 mmol) was added dropwise, with continuous stirring, over a 30 minute period. The solution was stirred for an additional 4 hours Solvent and unreacted trimethylsilylsulfonyl chloride were removed by distillation at reduced pressure. The resulting polymer, abbreviated as PSESO$_3$TMS, was a light brown, viscous liquid.

To a 200 mL saturated aqueous sodium bicarbonate solution, PSESO$_3$TMS was added dropwise with continuous stirring. After addition, the solution was concentrated on a rotary evaporator. To remove excess sodium bicarbonate, the product, sulfonated silicone PSESO$_3$Na, was purified by repeated dialysis using 1000 Mw cut-off membrane for 10 days. After that, the polymer was dried by azeotropic distillation with benzene and then kept in a vacuum over at 60° C. for 4 days.

Example 5

Sulfonated dimethylsiloxane copolymer V ($R^1$=CH$_2$, $R^2$=$R^4$=$R^{16}$=CH$_3$, $R^3$=Et, $R^{14}$=C$_6$H$_{13}$, q$\approx$50, p$\approx$2, n$\approx$48).

To a mixture of (50-55%) methylhydro—(45-50%) dimethylsiloxane copolymer (50CPS) (13.4 g, 100 mmol) and ETMA (21.4 g, 100 mmol) in 100 mL dry toluene, several drops of platinum divinyltetramethyldisiloxane solution (3% in xylene) was added. The mixture was heated at 60° C. for 48 hours. The extent of reaction was followed by IR spectroscopy. The remaining Si—H groups were reacted in a similar fashion for an additional 6 hours by adding a slight excess of 1-hexene. Solvent and unreacted BTDA were removed at reduced pressure and the resulting liquids were kept under high vacuum for 24 hours. The product, referred to as 50PSEA, was a light yellow, viscous liquid.

A 100 mL one-necked round bottomed flask was baked by flame and flushed with dry argon, then equipped with a magnetic stirring bar in a dry box. The flask was charged with 50 mL of anhydrous dichloroethane and ETMA modified copolysiloxane (10 g). Trimethylsilylsulfonyl chloride (6.42 g) was added dropwise, with continuous stirring, over a 30 minute period. The solution was stirred for an additional 6 hours Solvent and unreacted trimethylsilylsulfonyl chloride were removed by distillation at reduced pressure. The resulting polymer, abbreviated as 50PSESOTMS$_3$, was a light brown, viscous liquid.

To a 200 mL saturated sodium bicarbonate aqueous solution, 50PSESO$_3$TMS was added dropwise with continuous stirring. After addition, the solution was concentrated on a rotary evaporator. To remove excess sodium bicarbonate, the product, sulfonated copolysiloxane 50PSESO$_3$Na, was purified by repeated dialysis using 1000 Mw cut-off membrane for 10 days. After that, the polymer was dried by azeotropic distillation with benzene and then kept in a vacuum oven at 60° C. for 4 days.

Example 6

Sulfonated copolysiloxane V ($R^1$=CH$_2$, $R^2$=$R^4$=$R^{16}$= CH$_3$, $R^3$=Et, $R^{14}$=C$_6$H$_{13}$, q$\approx$30, n$\approx$68, p$\approx$2)

Following the same procedure, (30-35%) methylhydro—(65-70%) dimethylsiloxane copolymer (30 CPS) was sulfonated. The product, sulfonated copolysiloxane 30PSESO$_3$Na, was obtained as a white solid.

Example 7

Sulfonated polysiloxane V ($R^1$=CH$_2$, $R^2$=$R^4$=CH$_3$, $R^3$=Et, $R^{14}$=CH$_2$CH$_2$(C$_{10}$H$_{10}$Fe), $R^{16}$=C$_6$H$_{13}$, q$\approx$2, p$\approx$49, n$\approx$49)

To a mixture of PMHS (6 g, 100 mmol), vinylferrocene (10.6 g, 50 mmol) and ETMA (10.7 g, 50 mmol) in 100 mL dry toluene, several drops of platinum divinyltetramethyldisiloxane solution (3% in xylene) was added. The mixture was refluxed at 60° C. for 48 hours. The extent of reaction was followed by IR spectroscopy. The remaining Si—H groups were reacted in a similar fashion for an additional 6 hours by adding a slight excess of 1-hexene. Solvent and unreacted ETMA were removed at reduced pressure evaporator first, and the resulting liquids were kept under high vacuum for 24 hours. The ferrocene and silyl ketene acetal-modified siloxane copolymer (20 mmol) was dissolved in 50 mL anhydrous dichloroethane and then trimethylsilylsulfonyl chloride (10 mmol) was added dropwise, with continuous stirring, over a 30 minute period. The solution was stirred for an additional 4 hours. Solvent and unreacted trimethylsilylsulfonyl chloride were removed by distillation at reduced pressure. The resulting polymer was hydrolyzed in a saturated aqueous sodium bicarbonate solution. To remove excess sodium bicarbonate, the ferrocene-containing sulfonated silicone, FcPSESO$_3$Na, was purified by repeated dialysis using a 1000 Mw cut-off membrane for 10 days. The polymer was dried by azeotropic distillation with benzene, kept in a vacuum oven at 60° C. for 4 days, and obtained as a dark yellow solid.

Example 8

Sulfonated polysiloxane III ($R^1$=CH$_2$, $R^2$=$R^4$=CH$_3$, $R^3$=Et, $R^{12}$=(CH$_2$)$_3$CH(CH$_3$)COOEt, n$\approx$48, p$\approx$52)

It is contemplated that the desired polysiloxane can be synthesized in analogous fashion to that of earlier examples:

To a mixture of PMHS (6 g, 100 mmol) and ETMA (21.4 g, 100 mmol) in 100 mL dry toluene, several drops of platinum divinyltetramethyldisiloxane solution (3%) in xylene are added. The mixture is refluxed at 60° C.

for 48 hours. The extent of reaction is followed by IR spectroscopy. The remaining Si—H groups are reacted in a similar fashion for an additional 6 hours by adding a slight excess of 1-hexene. Solvent and unreacted ETMA are removed at reduced pressure and the resulting liquid is kept under high vacuum for 24 hours.

A 100 mL one-necked round bottomed flask is baked by flame and flushed with dry argon, then equipped with magnetic stirring bar in a dry box. The flask is charged with 50 mL anhydrous dichloroethane and silyl ketene acetal modified polysiloxane (20 mmol). After that, trimethylsilyl sulfonyl chloride (10 mmol) is added dropwise, with continuous stirring, over a 30 minute period. The solution is stirred for an additional 6 hours. Solvent and unreacted trimethylsilylsulfonyl chloride are removed by distillation at reduced pressure. The resulting polymers are abbreviated as p-PSESO$_3$TMS (p represents the partial sulfonation).

To a 200 mL saturated aqueous sodium bicarbonate solution, p-PSSO$_3$TMS is added dropwise with continuous stirring. After addition, the solution is concentrated on a rotary evaporator. To remove excess sodium bicarbonate, the product, sulfonated silicone nPSESO$_3$Na (or nPSBSO$_3$Na) is purified by repeated dialysis using 1000 Mw cut-off membrane for days. The polymer is dried by azeotroping with benzene and then kept in a vacuum oven at 60° C. for 4 days.

While the invention has been particularly shown and described with reference to preferred embodiments thereof, it will be understood by those skilled in the art that other changes in form and details may be made therein without departing from the spirit and scope of the invention.

We claim:

1. A compound of formula

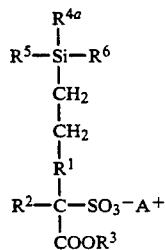

wherein
R$^1$ is phenylene, naphthylene, or linear or branched alkylene;
R$^2$ is hydrogen or lower-alkyl;
R$^3$ is alkyl;
R$^{4a}$ is lower-alkyl, lower alkoxy, or tri(lower-alkyl)-siloxy;
R$^5$ and R$^6$ are independently chosen from the group consisting of lower-alkyl, lower-alkoxy and

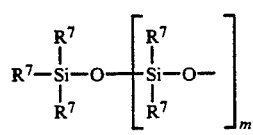

R$^7$ is lower-alkyl;
m is zero or an integer from 1 to 100; and
A$^+$ is hydrogen, alkali metal, ammonium or tetra(-lower-alkyl)ammonium.

2. A compound according to claim 1 wherein R$^{4a}$ and R$^7$ are methyl and R$^2$ is lower-alkyl.

3. A compound according to claim 2 wherein R$^2$ is methyl and R$^1$ is methylene.

4. A compound according to claim 3 wherein m is zero.

5. A compound of formula

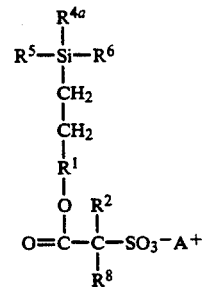

wherein
R$^1$ is phenylene, naphthylene or linear or branched alkylene;
R$^2$ is hydrogen or lower-alkyl;
R$^{4a}$ is lower-alkyl, lower-alkoxy, or tri(lower-alkyl)-siloxy;
R$^5$ and R$^6$ are independently chosen from the group consisting of lower-alkyl, lower-alkoxy and

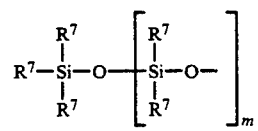

R$^7$ is lower-alkyl;
R$^8$ is hydrogen or alkyl;
m is zero or an integer from 1 to 100; and
A$^+$ is hydrogen, alkali metal, ammonium or tetra(-lower-alkyl)ammonium.

6. A compound according to claim 5 wherein R$^{4a}$ and R$^7$ are methyl and R$^2$ and R$^8$ are lower-alkyl.

7. A compound according to claim 6 wherein R$^2$ is methyl and R$^1$ is methylene.

8. A compound according to claim 7 wherein R$^8$ is methyl and m is zero.

9. A random copolymer of formula

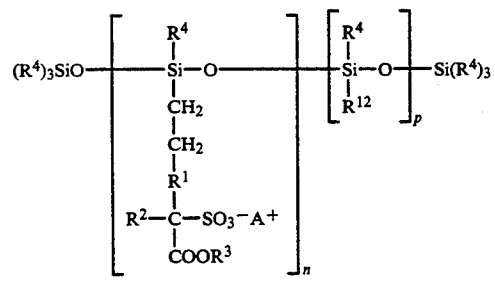

wherein
R$^1$ is phenylene, naphthylene or linear or branched alkylene;
R$^2$ is hydrogen or lower-alkyl;
R$^3$ is alkyl;
R$^4$ is lower-alkyl;

$R^{12}$ is lower alkyl or $CH_2CH_2R^{13}$ where $R^{13}$ is hydrogen, lower-alkyl, ferrocenyl, poly(alkyleneoxy) or $-R^1-CH(R^2)COOR^3$;

n is an integer from 2 to 2000;

p is zero or an integer from 1 to 2000; and $A^+$ is hydrogen, alkali metal, ammonium, or tetra(lower-alkyl)ammonium.

10. A random copolymer according to claim 9 wherein the ratio of n to p is about 48:52.

11. A random copolymer according to claim 10 wherein $R^2$ and $R^4$ are methyl.

12. A polymer according to claim 11 wherein $R^1$ is methylene, $R^3$ is ethyl, $R^{12}$ is $-CH_2CH_2CH_2CH(CH_3)COOEt$, n is about 39 and p is about 41.

13. A random copolymer according to claim 9 wherein the ratio of n to p is about 30:70.

14. A polymer according to claim 13 wherein $R^2$ and $R^4$ are methyl.

15. A polymer according to claim 14 wherein $R^1$ is methylene, $R^3$ is ethyl, $R^{12}$ is methyl, n is about 24 and p is about 56.

16. A polymer according to claim 9 wherein p is zero.

17. A polymer according to claim 16 wherein $R^2$ and $R^4$ are methyl.

18. A polymer according to claim 17 wherein $R^1$ is methylene, $R^3$ is ethyl and n is about 60 to 80.

19. A random copolymer of formula

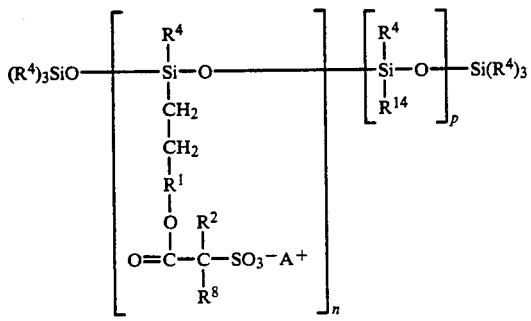

wherein $R^1$ is phenylene, napthylene or linear or branched alkylene;

$R^2$ is hydrogen or lower-alkyl;

$R^4$ is lower-alkyl;

$R^8$ is alkyl;

$R^{14}$ is lower alkyl or $-CH_2CH_2-R^{15}$ where $R^{15}$ is hydrogen, lower-alkyl, ferrocenyl poly(alkyleneoxy) or $-R^1-OC(O)CHR^2R^8$;

n is an integer from 2 to 2000;

p is zero or an integer from 1 to 2,000; and $A^+$ is hydrogen, alkali metal, ammonium or tetra(lower-alkyl)ammonium.

20. A random copolymer according to claim 19 wherein the ratio of n to p is about 48:52.

21. A random copolymer according to claim 20 wherein $R^2$ and $R^4$ are methyl.

22. A copolymer according to claim 21 wherein $R^1$ is methylene, $R^3$ is ethyl, $R^{13}$ is methyl, n is about 39 and p is about 41.

23. A random copolymer according to claim 19 wherein the ratio of n to p is about 30:70.

24. A copolymer according to claim 23 wherein $R^2$ and $R^4$ are methyl.

25. A copolymer according to claim 24 wherein $R^1$ is methylene, $R^3$ is ethyl, n is about 24 and p is about 56.

26. A polymer according to claim 19 wherein p is zero.

27. A polymer according to claim 26 wherein $R^2$ and $R^4$ are methyl.

28. A polymer according to claim 27 wherein $R^1$ is methylene, $R^3$ is ethyl and n is about 60 to 80.

29. A random copolymer of formula

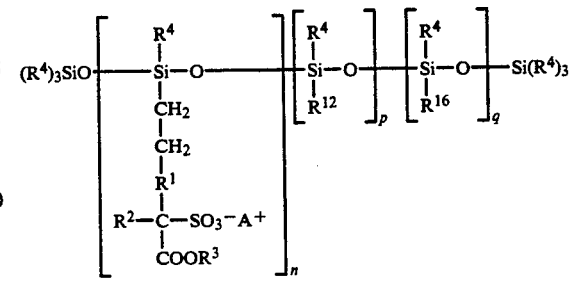

wherein $R^1$ is phenylene, napthylene or linear or branched alkylene;

$R^2$ is hydrogen or lower-alkyl;

$R^3$ is alkyl;

$R^4$ and $R^{16}$ are independently lower-alkyl;

$R^{12}$ is lower alkyl or $-CH_2CH_2-R^{13}$ where $R^{13}$ is hydrogen, lower-alkyl, ferrocenyl poly(alkyleneoxy) or $-R^1-CH(R^2)COOR^3$;

n and q are integers from 2 to 2000;

p is zero or an integer from 1 to 2,000; and $A^+$ is hydrogen, alkali metal, ammonium or tetra(lower-alkyl)ammonium.

30. A random copolymer according to claim 29 having the formula

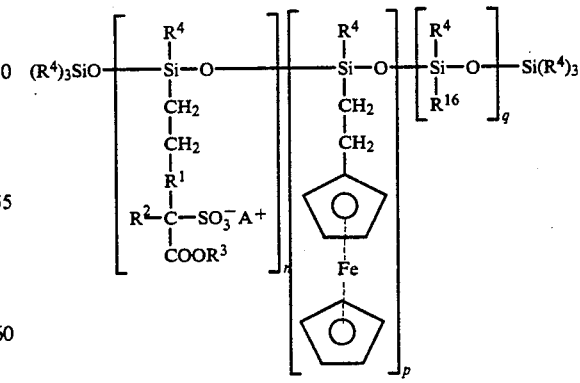

31. A polymer according to claim 30 wherein the ratio of n:p:q is 46:39:15, $R^1$ is methylene, $R^2$, and $R^4$, are methyl and $R^3$ is ethyl.

32. A random copolymer of formula

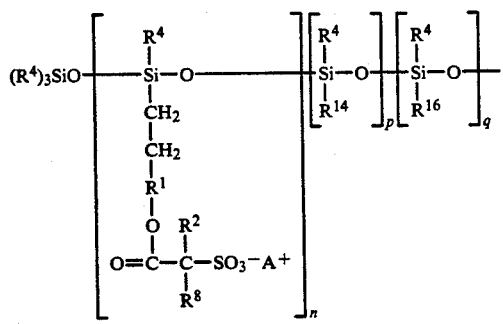

wherein
$R^1$ is phenylene, napthylene or linear or branched alkylene;
$R^2$ is hydrogen or lower-alkyl;
$R^8$ is alkyl;
$R^4$ and $R^{16}$ are independently lower-alkyl;
$R^{14}$ is lower alkyl or $CH_2CH_2R^{15}$ where $R^{15}$ is hydrogen, lower-alkyl, ferrocenyl poly(alkyleneoxy) or $-R^1-OC-(O)CHR^2R^8$;
n and q are integers from 2 to 2000;
p is zero or an integer from 1 to 2,000; and
$A^+$ is hydrogen, alkali metal, ammonium or tetra(-lower-alkyl)ammonium.

33. A random copolymer according to claim 32 having the formula

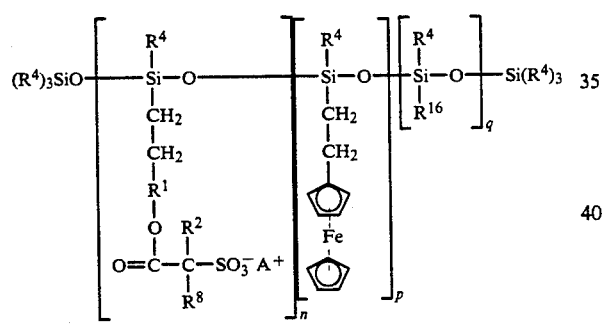

34. A polymer according to claim 33 wherein the ratio of n:p:q is 46:39:15, $R^1$ is methylene, $R^2$, and $R^4$, and $R^8$ are methyl.

35. A compound of formula

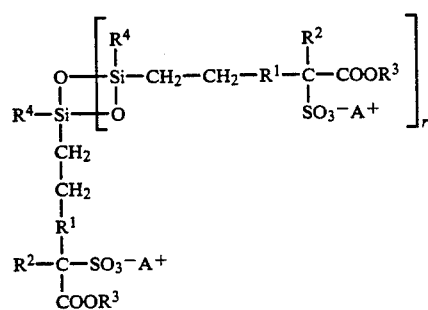

VII wherein
$R^1$ is phenylene, napthylene or linear or branched alkylene;
$R^2$ is hydrogen or lower-alkyl;
$R^3$ is alkyl;

$R^4$ is lower-alkyl;
r is an integer from 3 to 5; and
$A^+$ is hydrogen, alkali metal, ammonium or tetra(-lower-alkyl)ammonium.

36. A compound of formula

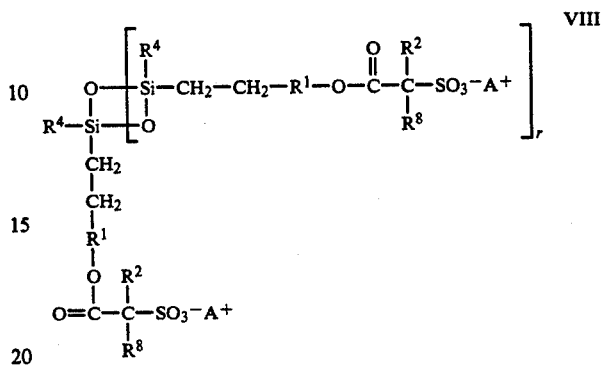

VIII wherein
$R^1$ is phenylene, napthylene or linear or branched alkylene;
$R^2$ is hydrogen or lower-alkyl;
$R^4$ is lower-alkyl;
$R^8$ is alkyl;
r is an integer from 3 to 5; and
$A^+$ is hydrogen, alkali metal, ammonium, or tetra(-lower-alkyl)ammonium.

37. A process for the preparation of sulfonated silicones comprising the steps of:
(a) reacting a silicone having Si—H bonds with an olefin-terminated (trialkyl silyl) ketene acetal of formula

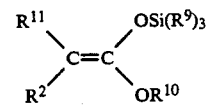

wherein
$R^2$ is hydrogen or lower-alkyl;
$R^9$ is lower-alkyl; and
one of
$R^{10}$ and $R^{11}$ is alkyl and the other is an olefin-terminal linear or branched alkylene, phenylene or naphthylene radical;
in the presence of a hydrosilylation catalyst to produce a silicone attached to said ketene acetal at the terminal carbon of said olefin-terminal radical $R^{10}$ or $R^{11}$;
(b) treating said ketene acetal attached to said silicone with a trialkylsily sulfonyl chloride to produce an α-trialkylsilysulfonyl ester; and
(c) hydrolyzing said α-trialkylsily sulfonyl ester with a mild base to provide a salt of an α-sulfonate.

38. A process according to claim 37 wherein said hydrosilylation catalyst is platinum divinyl tetramethyldisiloxane, said trialkylsilylsulfonyl chloride is trimethylsilylsulfonyl chloride, and said mild base is aqueous sodium bicarbonate.

39. A process for the preparation of sulfonated silicones comprising the steps of:
(a) reacting a silicone having Si—H bonds with an olefin-terminal α-trialkylsilylsulfonyl ester of formula

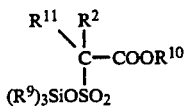

wherein
R² is hydrogen or lower-alkyl;
R⁹ is lower-alkyl; and
one of
R¹⁰ and R¹¹ is alkyl and the other is an olefin-terminal linear or branched alkylene, phenylene or naphthylene radical;
in the presence of a hydrosilylation catalyst to produce a silicone attached to said α-trialkylsily sulfonyl ester at the terminal carbon of said olefin-terminal radical R¹⁰ or R¹¹; and (b) hydrolyzing said α-trialkylsilylsulfonyl ester with a mild base to provide a salt of an α-sulfonate.

40. A process for the preparation of sulfonated silicones comprising the steps of:

(a) reacting a silicone having Si—H bonds with an olefin-terminated ester of formula XXII

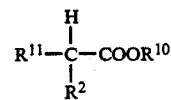

wherein R⁷ is hydrogen or lower-alkyl; and one of R¹⁰ and R¹¹ is alkyl and the other is an olefin-terminal linear or branched alkylene, phenylene or naphthylene radical, in the presence of a hydrosilylation catalyst to produce a silicone attached to the ester at the terminal carbon of the olefin-terminal radical R¹⁰ or R¹¹; and (b) treating the ester with a strong base followed by a trialkylsilyl halide to form a ketene acetal;

(c) treating the ketene acetal with a trialkylsilyl sulfonyl chloride to produce an α-trialkylsilyl-sulfonyl ester; and (d) hydrolyzing the α-trialkylsilyl sulfonyl ester with a mild base to provide a salt of an α-sulfonate.

* * * * *

UNITED STATES PATENT AND TRADEMARK OFFICE
CERTIFICATE OF CORRECTION

PATENT NO. : 5,326,890
DATED : Jul. 5, 1994
INVENTOR(S) : Wnek et al.

It is certified that error appears in the above-indentified patent and that said Letters Patent is hereby corrected as shown below:

Column 19, line 44 delete "napthylene" and substitute therefor "naphthylene".

Column 20, line 26 delete "napthylene" and substitute therefor "naphthylene".

Column 21, line 17 delete "napthylene" and substitute therefor "naphthylene".

Column 21, line 22 delete "$CH_2CH_{2R}15$" and substitute therefor "$CH_2CH_2R^{15}$".

Column 21, line 47 delete "and" between $R^2$, and $R^4$.

Column 21, line 65 delete "napthylene" and substitute therefor "naphthylene".

Signed and Sealed this

Second Day of May, 1995

BRUCE LEHMAN

Attest:

Attesting Officer

Commissioner of Patents and Trademarks